(12) United States Patent
Hennink et al.

(10) Patent No.: US 7,425,581 B2
(45) Date of Patent: Sep. 16, 2008

(54) TEMPERATURE SENSITIVE POLYMERS

(75) Inventors: Wilhelmus Everardus Hennink, Waddinxveen (NL); Cornelus Franciscus Van Nostrum, Vlijmen (NL); Marinus Jacob Van Steenbergen, Ede (NL); Osamu Soga, Ibaraki (JP)

(73) Assignee: Universiteit Utrecht, CS Utrecht ( * ) Notice: Subject to any disclaimer, the term of this patent is extended or adjusted under 35 U.S.C. 154(b) by 558 days.

(21) Appl. No.: 10/804,302

(22) Filed: Mar. 18, 2004

(65) Prior Publication Data

US 2004/0247670 A1 Dec. 9, 2004

Related U.S. Application Data

(63) Continuation-in-part of application No. 10/048,732, filed as application No. PCT/NL00/00542 on Jul. 28, 2000, now abandoned.

(30) Foreign Application Priority Data

Jul. 30, 1999 (EP) .................................. 99202523

(51) Int. Cl.
*A61K 47/00* (2006.01)
(52) U.S. Cl. .............. 514/772.1; 514/772.3; 514/772.4; 424/400; 424/489
(58) Field of Classification Search ........................ None
See application file for complete search history.

(56) References Cited

U.S. PATENT DOCUMENTS 5,939,453 A 8/1999 Heller et al.
6,497,903 B1 * 12/2002 Hennink et al. ............. 424/488
6,710,126 B1 * 3/2004 Hirt et al. .................... 525/61

FOREIGN PATENT DOCUMENTS

| EP | 0 693 508 | 1/1996 |
|---|---|---|
| FR | 2 676 451 | 11/1992 |
| WO | WO 92/07881 | 5/1992 |
| WO | WO 98/29461 | 7/1998 |

OTHER PUBLICATIONS

Neradovic et al., Macromolecules, 2003, 36, 7491-7498.*
Soga et al., Biomacromolecules 2004 5, 818-821.*
Soga et al "Physicochemical Characterization of Degradable Thermosensitive Polyeric Micelles" Langmuir, 2004, 20, 9388-9395.*

(Continued)

*Primary Examiner*—Michael G. Hartley
*Assistant Examiner*—Eric E. Silverman
(74) *Attorney, Agent, or Firm*—Morrison & Foerster LLP (57) ABSTRACT

The present invention relates to compositions comprising polymers whose solubility characteristics can be changed by incubation and particularly poly (N-(2-hydroxypropyl)methacrylamide mono/di-lactate) interpolymers. Another aspect of this invention is the application of such temperature sensitive polymers as release systems of biologically active compounds. The polymers of the present invention, comprise monomers which have modifiable functionality. The functionality of the monomers can for example be modified by the presence of hydrolysable groups. The modification is effected by the incubation, leading to a change of the water solubility characteristics of the polymer. The polymers used in the present invention contain hydrolysable chemical groups. As a result the polymer's solution characteristics, specifically its lower critical solution temperature (LCST), change upon incubation.

8 Claims, 3 Drawing Sheets

OTHER PUBLICATIONS

Soga et al. "Poly(N-(2-hydroxypropyl) Methacrylamide Mono/Di Lactate): A New Class of Biodegradable Polymers with Tuneable Thermosensitivity" Biomacromolecules, 2004, 5, 818-821.*
Cadee et al., Polymer (1999) 40:6877-6881.
Neradovic et al., Macromolecules (2001) 34:7589-7591.
Bankova, Eur. Polym. Journal (1997) 34(2):247-253.
Cammas et al., Journal of Controlled Release (1997) 48:157-164.
Crommelin et al., Advanced Drug Delivery Reviews (1995) 17:49-60.
Kwon et al., Langmuir (1993) 9:945-949.
Kwon et al., Pharmaceutical Research (1995) 12(2):192-195.
Van Dijk-Wolthuis et al., Polymer (1997) 38(25):6235-6242.
Yokoyama et al., Journal of Controlled Release (1998) 50:79-92.

* cited by examiner

TEMPERATURE SENSITIVE POLYMERS

CROSS-REFERENCE TO RELATED APPLICATIONS

This is a continuation in part of U.S. Ser. No. 10/048,732, filed on Jun. 13, 2002, which is a national phase filing of PCT/NL00/00542, filed Jul. 28, 2000, which claims priority to European patent application number 99202523.9, filed Jul. 30, 1999. The contents of these applications are incorporated herein by reference.

FIELD OF THE INVENTION

The invention relates to compositions comprising polymers whose solubility characteristics can be changed by incubation. Another aspect of this invention is the application of such temperature sensitive polymers as release systems of biologically active compounds. In yet a further aspect, the invention relates to a novel class of polymers with tuneable thermosensitivity, which polymers are biodegradable forming degradation products that are either endogenous or non-toxic in the human or animal system.

The fast developments in the field of molecular biology and biotechnology have made it possible to produce a large number of pharmaceutically interesting products in large quantities. For instance, pharmaceutically active peptides and proteins can suitably be used as drugs in the treatment of life-threatening diseases, e.g., cancer, and of several types of viral, bacterial and parasital diseases; in the treatment of, e.g., diabetes; in vaccines, e.g., for prophylactic aims; for anti-conception purposes, and so on and so forth. Especially the specialized biological activities of these types of drugs provide tremendous advantages over other types of pharmaceutics. Also low molecular weight pharmaceuticals, such as cytostatics, antibiotics, etc., can be produced in large amounts.

Recent statistics show that the FDA approved 130 biotechnology derived protein medicines and vaccines (Crommelin, et al. Shifting paradigms: biopharmaceuticals versus low molecular weight drugs, *Int J Pharm* (2003) 266:3-16).

Examples of (recombinant) proteins, which are considered very interesting from a pharmacological point of view, are cytokines, such as interleukins, interferons, tumor necrosis factor (TNF), insulin, proteins for use in vaccines, and growth hormones.

Due to their nature, proteins and proteinaceous products, including peptides, which group of products will be referred to as protein drugs herein-below, cannot be administered orally. These products tend to degrade rapidly in the gastrointestinal tract, in particular because of the acidic environment and the presence of proteolytic enzymes therein.

Moreover, to a high extent protein drugs are not able to pass endothelial and epithelial barriers, due to their size and, generally, polar character.

For these reasons, protein drugs have to be brought in the system parenterally, i.e., by injection, however, the pharmacokinetical profile of these products is such that injection of the product per se requires a frequent administration. For, it is a known fact that proteinaceous material is eliminated from the blood circulation within minutes.

In other words, since protein drugs are chemically and/or physically unstable and generally have a short half-life in the human or animal body, multiple daily injections or continuous infusions are required for the protein drug to have a desired therapeutic effect. It will be evident that this is inconvenient for patients requiring these protein drugs. Furthermore, this type of application often requires hospitalization and has logistic drawbacks.

In addition, it appears that at least for certain classes of pharmaceutical proteins, such as cytokines which are presently used in, e.g., cancer treatments, the therapeutic efficacy is strongly dependent on effective delivery, e.g., intra- or peritumoral. In such cases, the protein drugs should be directed to the sites where their activity is needed during a prolonged period of time.

Hydrogel systems for controlled or sustained release are very desirable for such purposes.

Moreover, low molecular weight drugs, e.g., cytostatics such as paclitaxel, should be targeted towards specific sites in a body. Suitable drug targeting systems for targeted release are, e.g., micellar structures for release of low molecular weight drugs.

Hence, there is a need for delivery systems which have the capacity for sustained, controlled and/or targeted release. In the art, delivery systems comprising soluble polymers have been proposed. Such delivery systems can be obtained by using such soluble polymers for example in the form of microparticles in which the protein drug is encapsulated. The polymer can be present throughout each microparticle, with the protein drug captured within the different polymer molecules. Alternatively, the polymer forms the outer membrane of the microparticle which contains the protein drug. However, in vitro or in vivo application of such systems have some inherent drawbacks. First, organic solvents have to be used to encapsulate proteins in the microparticles. Second, acidic products are frequently formed during degradation, which might result in a lowering of the pH. Both a low pH and organic solvents can affect protein stability. Furthermore, it appears to be difficult to control the protein release from these systems, which can lead to a burst release (see in this respect Van de Weert, et al. Protein instability in poly(lactic-co-glycolic acid) microparticles, *Pharm Res* (2000) 17:1159-1167).

The present inventors have now found that the use of temperature sensitive polymers, and especially those with a lower critical solution temperature, has a number of advantages.

Figure 1:
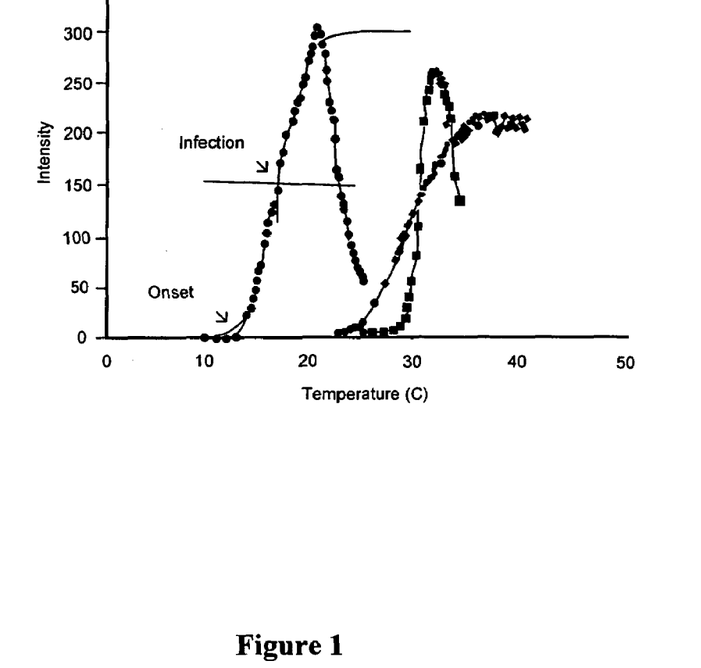
FIG. 1 shows a light scattering curve, wherein both the temperature at the point of inflection and the onset temperature are marked.

Temperature sensitive (or thermosensitive) polymers with a lower critical solution temperature (LCST) are presently under investigation for biomedical and pharmaceutical applications. Thermosensitive polymer having a LCST are remarkable materials, in that below this temperature such polymers are soluble, and above it they precipitate. The lower critical solution temperature can be defined as the temperature at the point of inflection in a graph representing the amount of solids in the sample (for example as measured using light scattering techniques) vs. temperature. Alternatively, the LCST can be defined as the lowest temperature where precipitated polymer particles are detected (the 'onset' temperature). An example of a light scattering curve is shown in FIG. 1. Both the temperature at the point of inflection and the onset temperature are marked. Unless otherwise indicated, in the present description LCST is defined by the point of inflection.

Thermosensitive polymers with LCST are soluble in aqueous solutions below the cloud point (CP), but precipitate above this temperature due to the dehydration of the polymer chains.

LCST-polymers can be used advantageously as drug release systems, because their preparation can be carried out at a temperature which is lower than the temperature at which the release is to be effected, for example the body temperature. Since the temperature can be kept low, there is little risk of denaturation or degradation of the (protein) drug to be released. Another important advantage of the use of LCST-polymers in drug release systems is that the loading of the drug delivery system can be accomplished in an aqueous system, avoiding the use of toxic organic solvents. In addition, the LCST-polymers can be chosen such that they are degradable and/or can easily be excreted by the kidneys, once in soluble form.

BACKGROUND ART

The use of LCST polymers as controlled release systems is, e.g., known from U.S. Pat. No. 5,720,976. In this publication release systems are disclosed, wherein an active ingredient is encapsulated in liposomes. LCST polymers are grafted to the surface of liposomes. By choosing the ratio of respective monomers in the LCST polymers, the LCST value of the polymers can be adjusted.

Furthermore, WO-A-92/07881 discloses that the solubility of polyacrylamide changes as a result of the presence of amide groups, which groups have a buffering effect. This pertains to the solubility per se, not to the LCST, which is not mentioned in this publication.

Also in EP-A-0 693 508 and in DE-A-4 023 578, it is described that the temperature sensitivity of certain polymers can be influenced by varying the ratio of the comonomers present in these certain polymers.

None of these prior art documents teach or suggest however, that LCST polymer systems can be modified, as is done in accordance with the present invention in such a way, that the LCST value of the polymers changes during incubation and as a result of incubation, and by which the above mentioned advantages of the present invention can be obtained.

DESCRIPTION OF THE INVENTION

The LCST-polymer systems of the present invention can be used for drugs-targeting by incorporation into the matrix of compounds which makes the system suitable for physico-chemical or physical homing strategies. Such strategies may employ a homing device, which is a characteristic protrusion on a particle, capable of recognizing the target cell or tissue. Examples of such homing devices are monoclonal antibodies or fragments thereof, growth factor, insulin, sugar moieties, transferrin, etc. In the physico-chemical strategy, homing devices are designed such that they only recognize and interact with specific structures on the surface of target cells or tissues. In the physical strategy, homing devices are designed to accumulate at target sites by physical means, such as a local magnetic field or heat. See for example D. J. A. Crommelin, et al., *Adv. Drug. Deliv. Rev.* (1995) 17:49-60.

The protein drug delivery systems based on LCST-polymers can be prepared conveniently by introduction of the protein drug into the polymer matrix. This is obtained by mixing the protein drug with the polymer, which is in dissolved state, for example because it is below its LCST. Subsequently, the mixture is brought in a state in which the polymer precipitates, for example by bringing it above its LCST, by which process the protein drug is captured within the precipitating polymer matrix, thus yielding a drug delivery system.

For the use in protein drug delivery systems, it is essential that the LCST-polymer to be applied is not below or above its critical solubility temperature. Effective application as controlled release system can only be obtained when the in vivo temperature is just below the critical solution temperature. Although it is known in the art—see, e.g., the above discussed publications—that LCST-polymers can be modified by changing their composition, it will be clear that a choice with respect to the LCST has to be made prior to the administration. Once a certain polymer is chosen, its LCST is fixed. Variations of the application temperatures, as can occur easily for example as a result of differences or variations in body temperature, can lead consequently to different and non-gradual release profiles.

Said in other words, for biomedical and pharmaceutical applications of thermosensitive polymers, it is important to have possibilities to control the CP around body temperature. Furthermore, polymers of which the CP increase from below to above body temperature in time are very attractive materials, because, e.g., the controlled release of drugs without thermal treatment is feasible using such polymers.

The present invention provides a polymer that is suitable for use in a controlled release system. Consequently, this polymer can be applied as a controlled release system having all the aforementioned advantages.

The present inventors have found that when certain water soluble polymers are chemically modified, their critical solution temperature will vary in situ, viz. upon in vivo or in vitro application in an aqueous environment. These changes are time dependent. In this description and the appending claims, application in an aqueous environment, under conditions enabling the reactions that result in the change of critical temperature, for example as a result of hydrolysis, is referred to as incubation. It is also possible that the incubation is effected by enzymes present in the aqueous environment.

The polymer of the present invention comprises monomers which have modifiable functionality. The functionality of the monomers can for example be modified by the presence of hydrolysable groups. The modification is effected by the incubation, leading to a change of the water solubility characteristics of the polymer.

When reference is made to a polymer in this description, also homopolymers, copolymers, terpolymers, graft polymers, (highly) branched polymers and other interpolymers are to be understood. In fact, copolymers and terpolymers have the additional advantage that they provide an extra parameter affecting the final result, since different monomers, having different solubility characteristics, can be incorporated in one polymer, as to adjust the solubility characteristics (such as the solubility itself or the temperature dependency of the solubility) of the resulting copolymer. Copolymers and terpolymers thus form a preferred embodiment of the present invention.

The polymer according to the present invention is obtained by choosing the properties of the monomers such that upon incubation the functionality of the monomers changes and as a result the solubility and/or the temperature dependency of the solubility of the entire polymer, changes.

In a particular embodiment, the monomers are chosen so that their hydrophilicity changes upon incubation. As a result, the hydrophilicity of the entire polymer will change upon incubation. This will lead to a polymer with a different solubility and/or temperature dependency of the solubility.

In the copending parent application, it is specifically disclosed that a temperature sensitive polymer can be obtained by choosing a monomer that is suitable for the envisaged application, e.g., a monomer that forms a pharmaceutically acceptable polymer. Suitable monomers are the monomers selected from the group comprising ethylene glycol, lactic acid, acrylamide, methacrylamide, acrylic acid, and derivates and substituted species thereof. These monomers and/or other monomers are then reacted under suitable conditions to form homopolymers of one of these monomers or copolymers, terpolymers or other polymers of two or more monomers.

Preferred monomers are N-isopropyl acrylamide (NIPAAm), 2-hydroxyethyl methacrylate (HEMA), 2-hydroxyethyl acrylate (HEA), acrylamide (AAm), glyceryl methacrylate or glycidyl methacrylate (GMA), glyceryl acrylate or glycidyl acrylate (GA), hydroxypropyl methacrylamide (HPMAAm), dimethyl-aminoethyl methacrylate (DMAEMA) and dimethylaminoethyl acrylate (DMAEA).

In a preferred embodiment of the invention described in the copending parent application, the change of solubility characteristics is effected by hydrolysis of a group present on at least one of the monomers that form the polymer. Such a group is preferably chosen from ester, amide, carbonate, carbamate, and anhydride groups. Even more preferably such a group comprises a lactate unit, such as a monolactate, a dilactate or an oligolactate group. In case of in vivo application such a group can advantageously be an enzymatically or chemically hydrolyzable group. The ester groups are introduced in the polymer by choosing suitable monomers as a starting material, such as 2-hydroxyethyl methacrylate-monolactate. The monomers can be provided with ester groups by techniques known to the person skilled in the art.

MODES OF CARRYING OUT THE INVENTION

In the copending parent application the preferred embodiment was based on poly(N-isopropylacrylamide) (PNIPAAm), which has its CP around 32° C. in water. It is the most extensively studied thermosensitive polymer and is used for the design of thermosensitive drug delivery systems such as polymeric micelles and hydrogels. This polymer has also been used to modify the surface properties of liposomes. The CP of PNIPAAm can be modulated by copolymerising with hydrophobic or hydrophilic comonomers: hydrophobic comonomers decrease the CP whereas hydrophilic comonomers have the opposite effect.

The most preferred thermosensitive polymers of the parent application are thermosensitive copolymers of NIPAAm and N-(2-hydroxypropyl)methacrylamide lactate (poly (NIPAAm-co-HPMAm-lactate)) and their block copolymers with poly(ethylene glycol) (poly(NIPAAm-co-HPMAm-lactate)-b-PEG). When ≧35 mol % HPMAm-lactate was copolymerised with NIPAAm, these polymers had their CP below body temperature, whereas after hydrolysis of the lactate side chain the CP increased above 37° C. As a result, polymeric micelles formed with poly(NIPAAm-co-HPMAm-lactate)-b-PEG showed controlled instability at body temperature.

Upon further investigation, the present inventors have realized that the biodegradability of PNIPAAm should be improved. Moreover, the biocompatibility of PNIPAAm is not well-known at present. In their investigations, the present inventors have found that a favorable system can be based on (HPMAm-lactate based polymers). The present invention is therefore based on a novel class of thermosensitive and biodegradable polymers and particularly on homopolymers of a (N-2-hydroxypropyl)methacrylamide lactate and preferably of N-(2-hydroxypropyl)methacrylamide dilactate (HPMAm-dilactate) or interpolymers of HPMAm-dilactate, and especially poly(N-(2-hydroxypropyl)methacrylamide mono/di lactate) (poly(HPMAm-mono/di lactate)).

In the present description and the appending claims, the term "interpolymer" refers to a polymer comprising at least two types of monomers, and hence encompasses copolymers, terpolymers, etc.

Preferably, the invention relates to homopolymers of HPMAm-dilactate and other hydrophilic monomers such as HPMAm-monolactate, HPMAm-(lactate)$_n$, wherein n is an integer from 3 to 10, preferably from 3 to 5; HPMAm; or hydroxy($C_{1-6}$ alkyl)methacrylate. Also terpolymers of poly (HPMAm-mono/dilactate) and a further hydrophilic monomer are suitable to be used.

The cloud points (CP) of poly(HPMAm-monolactate) and poly(HPMAm-dilactate) in water were 65° C. and 13° C., respectively. The lower CP for poly(HPMAm-dilactate) is likely due the greater hydrophobicity of the dilactate side group over the monolactate side group. The CP of poly(HPMAm-monolactate-co-HPMAm-dilactate) increased linearly with the mole percentage of HPMA-monolactate, which demonstrates that the CP is tuneable by the copolymer composition.

Hence, in a first aspect, the present invention relates to a temperature sensitive polymer having a lower critical solution temperature that changes during incubation in an aqueous solution or medium, which polymer is a homo- or interpolymer of a (N-(2-hydroxypropyl)methacrylamide lactate). In a preferred embodiment said N-(2-hydroxypropyl)methacrylamide lactate is the mono- or dilactate, more preferably the dilactate.

Preferably, the polymer of the invention has a lower critical solution temperature before incubation below mammalian body temperature and a LCST after incubation above mammalian body temperature. In the most preferred embodiment, this mammalian body temperature is human body temperature, i.e., about 37° C.

The term "mono/dilactate" means that part of the monomers used in the polymers of the invention are in the monolactate form, and part or all of the monomers used in the polymers of the invention are in the dilactate form.

Due to the hydrolysable lactic acid side groups the CP will increase in time with lactic acid, an endogenous compound, and the water-soluble pHPMAm as degradation products. pHPMAm is a well-known non-toxic macromolecular carrier which is, among others, used for the development of polymeric prodrugs of cytostatic agents. A good biocompatibility of poly(HPMAm-lactate) is expected, especially because PHPMAm systems have recently entered into clinical trials.

The polymer can be synthesized by starting from a mixture of the monomers and carrying out the polymerization reaction. It is also possible to first produce the polymer and subsequently functionalize it by coupling suitable groups. Compositions according to the present invention comprise block copolymers or terpolymers, random copolymers or terpolymers, random copolymers and polymeric networks, all of which polymers can be grafted, and mixtures thereof.

The solubility characteristics of the compositions according to the present invention will change upon incubation, for example when contacted with aqueous media, such as will be the case in in vivo application.

For application in mammals, the polymers according to the present invention have a critical temperature for both the composition as synthesized and the composition after incubation which is around body temperature, viz. between about 20 to 45° C., preferably between 30 and 42° C., and most preferably between 36 and 38° C. However, more preferably the value of LCST crosses the normal human body temperature (which is typically 37° C.) upon incubation so that the LCST before incubation is below 37° C., preferably below 35° C., and LCST after incubation is above 37° C., preferably above 38° C.

A preferred embodiment of the present invention is the use of the temperature sensitive polymer in or as a controlled release system which further comprises an active ingredient. Such systems are for example suitable for the controlled administration of drugs, such as protein drugs.

The controlled release system of the present invention can be used for the release of biologically active compounds, such as pharmaceutic compounds, e.g., pharmaceutically active peptides and proteins, genetic material e.g., nucleotides, RNA and DNA, plasmid DNA, anti-sense oligonucleotides, nutrients, low molecular drugs, etc. As mentioned above, hydrogels are especially suitable for the release of proteins and similar compounds, whereas micellar systems are suitable as carriers for low molecular weight drugs.

When the system is used for the delivery of genetic material, e.g., the delivery of plasmid DNA or anti-sense oligonucleotides, the LCST polymer of the invention preferably comprises cationic groups, such as DMAEMA.

It is also possible to make the controlled release systems which can be obtained by the present invention in the form of polymeric micelles. Polymeric micelles can be formed by the synthesis of amphiphilic blockcopolymers, e.g., AB block copolymers of PEG and poly(HPMAm-dilactate). In aqueous solutions, these polymers form micelles with a size of around 20 nm similar to those of the method of G. S. Kwon, et al., *Langmuir* (1993) 9:945-949). The hydrophobic core of these micelles can be loaded with drugs, e.g., the anti-cancer agent adriamycin. After in vivo administration of the these systems the adriamycin loaded micelles selectively accumulate in certain tumors, simultaneously releasing the drug, which results in killing of tumor cells (cfr. M. Yokoyama, et al., *J. Controlled Release* (1998) 50:79-92).

Polymers with an LCST have also been applied to design polymeric micelles. Below the LCST, the thermosensitive polymer acts as hydrophilic part of the system (e.g., in AB blockcopolymers of HPMAm-dilactate and styrene; cfr. S. Cammas, et al., *J. Controlled Release* (1997) 48:157-164).

Also, systems have been described in which PNIPAA forms the hydrophobic part of the polymeric micelle (in block copolymers of poly(ethylene glycol) and poly(N-isopropylacrylamide); M. D. C. Topp, et al., *Macromolecules* (1997) 30:8518-8520). After administration of these drug loaded PNIPAA systems and arrival at the target site, drug release can then be triggered by local hypothermia. Hypothermia is, however, not easily done or technically feasible for all tissues and organs, which limits the applicability of these systems.

These disadvantages can be overcome by using polymers composed of a hydrophilic block covalently linked to a block composed of thermosensitive polymer with hydrolyzable side groups. Such a hydrophilic block preferably comprises poly(ethyleneglycol) (PEG). When the LCST of the thermosensitive block is initially below body temperature, polymeric micelles are formed at 37° C. Due to hydrolysis of the side groups present in the thermosensitive block of the system, the LCST will increase, resulting in destabilization of the micelle when the LCST passes 37° C. When a drug is incorporated in the hydrophobic core, its release will be affected by this process. These systems can be favorably applied in, e.g., cancer treatment, treatment of rheumatism, arthritis, infections and/or inflammations.

As mentioned above, the polymers of the present invention comprise all possible polymer architectures, such as (multi-) block copolymers (such as AB, ABA, ABAB, etc.) or graft copolymers, random copolymers or terpolymers, or a polymeric networks; all of which may be grafted.

AB blockcopolymers with a thermosensitive block A (e.g., a block of the polymer of the invention) and a water-soluble B block (e.g., PEG) that form micelles when the LCST is passed, can be obtained by any known technique in the art for making AB blockcopolymers. Conveniently, these polymers are prepared using a so called macroinitiator.

A macroinitiator is a macromolecular initiator that is formed, e.g., by coupling a low molecular weight initiator, such as 4,4'-azobis(4-cyanopentanoic acid), (HO—CO—$CH_2$—$CH_2$_C($CH_3$)(CN)—N=$)_2$ (ABCPA), via its carboxyl groups at to the terminal OH group of a compound such as methoxylated PEG (i.e., $CH_3$—O-PEG-OH). In this way a compound of the formula ($CH_3$—O-PEG)$_2$-ABCPA is formed. Typically, PEG with a Mw of about 1500-10000, is used for this purpose. Preferably PEG with a Mw of about 5000 (PEG 5000) is used to form a (PEG 5000)$_2$-ABCPA macroinitiator. When this initiator decomposes by heat, a PEG chain with one radical is formed. This radical subsequently initiates the polymerization of monomers (such as HPMA-mono and dilactate, as described hereinbelow), by which an AB block copolymer is formed. In aqueous solution such polymers form a micellar structure when the temperature rises above its LCST. These micelles destabilize when the hydrolysis results in an A block with an increased LCST (above the temperature at which the micelles are applied, preferably at body temperature).

Alternatively, ABA block copolymers may be synthesized via the macroinitiator route by using instead of a monofunctional (i.e., α-methoxy) PEG or equivalent thereof, an α-ω-hydroxyl derived macroinitiator, viz. a polyester macroinitiator which has the ABCPA-groups alternating with PEG groups. When this initiator decomposes by heat, PEG chains with two radicals are formed. These radicals subsequently initiate the polymerization of monomers (such as HPMA-mono and dilactate), by which an ABA block copolymer is formed. The ABA block copolymers formed by this route will be soluble in water below the LCST. When the temperature is risen above the LCST of block A, a phase separated system will be formed, wherein as a result of the choice of block copolymer architecture, a hydrogel will be obtained. This hydrogel will dissolve gradually when the LCST of block A increases to above 37° C., due to the hydrolysis of the groups present on the monomers of this block. These systems are especially suitable for immobilizing cells, which can be employed in biotechnology and tissue engineering. Like the other systems mentioned hereinabove, these macroinitiator systems can also be used as matrix for controlled release of active ingredients, in particular pharmaceutical proteins.

It is noted, however, that also the ABA block copolymers—like the AB block copolymers—may also be prepared by other, conventional synthesis routes.

In Examples 3 and 4 herein-below, the synthesis of AB and ABA block copolymers are illustrated.

The controlled release system of the present invention may be in the form of a hydrogel. The hydrogel may comprise an ABA block copolymer wherein block A is a temperature sensitive polymer according to the invention and B is a hydrophilic polymer and preferably it is PEG. Such ABA block copolymers and hydrogels have the advantages described above.

When the polymers of the present invention are used for targeting drug purposes, the release system is made of particles, which particles have an average diameter of less than 1 μm, preferably less than 100 nm. To be of practical value, these particles will usually have to be larger than several nm, e.g., greater than 10 nm.

The ratio of different monomers and especially the mono/dilactate ratio which constitute the interpolymer of the invention, will influence the LCST and its development upon incubation. Generally for practical application, e.g., application in mammals, it is desirable to choose the ratios such that the LCST before incubation is below body temperature and after incubation above body temperature. The optimal ratio of each of the monomers will consequently depend strongly on the materials used and the envisaged application. The optimal values can be determined experimentally, as will be illustrated in the Examples hereinafter.

An important aspect of the present invention is the use of hydrolysable chemical groups in a temperature sensitive polymer in order to change said polymer's solution characteristics, specifically its critical solution temperature, more specifically its lower critical solution temperature (LCST).

It will be understood that apart from changing the solubility of polymers having a lower critical solution temperature, this can also be applied to polymers having a higher critical solution temperature, viz. polymers which dissolve at temperatures higher than their critical temperature, and precipitate at temperatures lower than this critical temperature.

The effect of the incubation can be an increase as well as a decrease of the critical temperature upon incubation.

The controlled release systems of the present invention can be prepared by the synthesis of a water soluble polymer. This is, e.g., done by a) functionalizing a monomer with hydrolysable groups, b) mixing of said monomer with at least one monomer of a different type in a suitable ratio using a suitable solvent in the presence of an initiator and/or a catalyst to form said polymer c) removing said solvent and dissolving the polymer, and d) precipitating said polymer; in which process the functionalizing of the monomers of step a) is optionally carried out after step b) on the monomers as they are present in the polymer; and subsequently mixing said water soluble polymer with a releasable compound.

Other suitable initiators as well as the catalysts for step a) are known in the art. An example of a suitable initiator is α,α'-azoisobutyronitrile (AIBN). An example of a suitable catalyst is stannous octoate ($SnOct_2$).

The polymer of the present invention comprises N-(2-hydroxypropyl)methacrylamide mono, dilactate and higher lactate (n=3-10) units. HPMAm can be synthesized as described by Oupialy, et al. (D. Oupicky, et al. DNA complexes with block and graft polymers of N-2-hydroxypropyl)methacrylamide and 2-(trimethylammonio)ethyl methacrylate. *J. Biomater. Sci. Polymer Ed.* (1999) Vol. 10, No. 5:573-590.

HPMAm can subsequently be esterified to mono, dilactate and higher lactate with lactide as described by Neradovic. D, et al. Degradation mechanism and kinetics of thermosensitive polyacrylamides containing lactic acid side chains. *Macromolecules* (2003) 36:7491-7498.

In principle, other monomers can be present as well. All monomers that copolymerize with HPMA (lactate) are suitable. Examples of these are acrylates, methacrylates, acrylamides, methacrylamide, N-vinyl-pyrrolidone, vinyllactates, vinylethers, etc. The amount of these comonomers that can be present will vary upon the specific monomers in question and is from 0-70 mole %, preferably from 0-50 mole %. The critical issue is the LCST behavior, which should be maintained.

A specific polymerization reaction giving the polymers of the invention is described hereinbelow in Example 1.

Apart from application as a controlled release agent, the polymers of the present invention can be applied as release systems for a variety of compounds in different applications, such as enzymes, colorants or other additives in laundry applications, adhesives in glues, insecticides or nutrients in agricultural applications, etc. Also possible is the use for the entrapment of living cells for, e.g., tissue engineering (see, in this respect, Lee, K. Y., and Mooney, D. J., "Hydrogels for tissue engineering," *Chemical Reviews* (2001) 101:1869-1879). Further possible applications are the topical administration polymers of the present invention loaded with active ingredients, e.g., for the treatment of burns. The polymers of the invention can also be used for the delivery of genetic material (DNA delivery).

The present invention will now be illustrated in the following Examples, which illustrate, but do not limit the invention.

EXAMPLE 1

Figure 2:
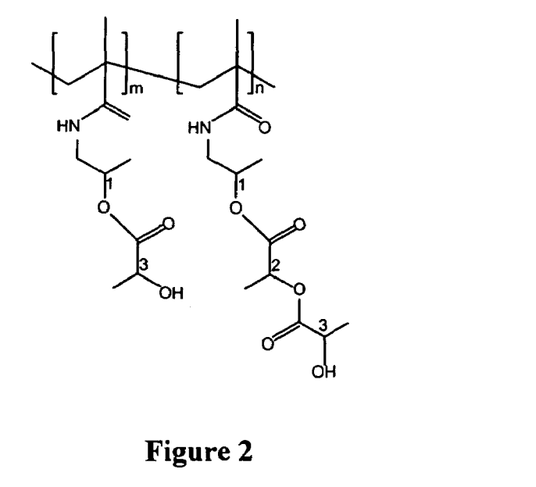
FIG. 2 gives the structure of poly(HPMAm-monolactate) (n=0), poly (HPMAm-dilactate) (m=0) and poly (HPMAm-dilactate) (m=0) and poly (HPMAm-monolactate-co-HPMAm-dilactate) (m, n=0).

Synthesis of poly(HPMAm-monolactate), poly(HPMAm-dilactate) and their Copolymers HPMAm-monolactate and HPMAm-dilactate were dissolved at a concentration of 0.1 g/mL in 1,4-dioxane. The HPMAm-monolactate/HPMAm-dilactate ratios were 100/0, 75/25, 50/50, 25/75, 0/100 (mol/mol). α,α'-Azoisobutyronitrile (AIBN) (total amount of monomers/AIBN is around 40/1 (mol/mol)) was added as radical initiator and the polymerization was conducted at 70° C. for 24 h in a nitrogen atmosphere. The polymers were collected by centrifugation after precipitation in diethyl ether. The polymers were further purified by dissolving them in cold water, followed by filtration through a 0.22 μm filter. After freeze-drying, the products were characterized by $^1$H NMR (solvent: $CDCl_3$) and gel permeation chromatography (GPC). GPC was done using Plgel 3 μm MIXED-D+Plgel 3 μm MIXED-E columns (Polymer Laboratories) and poly(ethylene glycol) standards. The eluent was DMF containing 10 mM LiCl, the elution rate was 0.7 mL/min. and the temperature was 40° C. The copolymer composition of the polymers was determined by $^1$H NMR from the ratio of the integral of the peak at 5.0 ppm (15.0, methine protons 1 and 2, FIG. 2) to the integral of the peak at 4.3 ppm ($I_{4.3}$, methine protons 3, FIG. 2) by the following formula: $I_{5.0}/I_{4.3}=1+x$, where x represents the molar fraction of HPMAm-dilactate in the copolymer.

The CP of the polymers was determined with static light scattering (SLS) using a Horiba Fluorolog® fluorometer (650 nm, at a 90° angle). The polymers were dissolved in water or in isotonic 120 mM ammonium acetate buffer (pH=5.0) at 0° C. The polymer concentration was varied between 0.1 mg/mL and 5 mg/mL. The scattering intensity was measured every 0.2° C. during heating and cooling (the heating/cooling rate was approximately 1° C./min). Onsets on the X-axis, obtained by extrapolation of the intensity-temperature curves during heating to intensity zero were considered as the CP. The CP determinations were done at least two times and the deviations were smaller than 0.5° C.

The results of the Example are discussed herein-below.

Poly(HPMAm-monolactate), poly(HPMAm-dilactate) as well as their copolymers (FIG. 2) were synthesized by radical polymerization. Five polymers with different monomer compositions were obtained in a yield between 50 and 70% (see Table 1).

TABLE 1

Characteristics of the polymers prepared in Example 1

| | Feed ratio (mol/mol) | Ratio in polymer[a) (mol/mol) | $M_n$[b) | $M_w$[b) | $M_w/M_n$ | CP (° C.)[c) | CP (° C.)[d) |
|---|---|---|---|---|---|---|---|
| poly(HPMAm-monolactate) | 100/0 | — | 11400 | 24400 | 2.14 | 65.0 | 63.0 |
| poly(HPMAm-monolactate-co-HPMAm-dilactate) | 75/25 | 75/25 | 7500 | 17600 | 2.35 | 50.5 | 47.5 |
| | 50/50 | 51/49 | 8100 | 16900 | 2.08 | 36.5 | 34.0 |
| | 25/75 | 26/74 | 6800 | 14000 | 2.06 | 25.0 | 23.0 |
| poly(HPMAm-dilactate) | 0/100 | — | 6300 | 10700 | 1.70 | 13.0 | 10.5 |

[a)Determined by $^1$H NMR.
[b)$M_n$ = number average molar weight; $M_w$ = weight average molar weight determined by GPC
[c)Determined by SLS for 1 mg/mL solution in water.
[d)Determined by SLS for 1 mg/mL solution in isotonic 120 mM ammonium acetate buffer (pH = 5.0).

Figure 3:
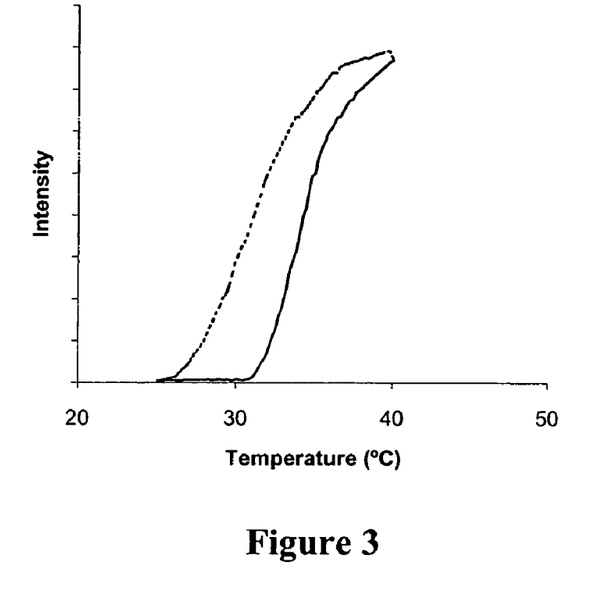
FIG. 3 shows a light scattering intensity temperature curve for poly (HPMAm-monolactate-co-HPMAm-dilactate) in isotonic 120 mM ammonium acetate buffer (pH=5.0) at 5 mg/ml. The molar ratio of HPMAm-monolactate to HPMAm-dilactate is 51:49 (mol/mol).
Figure 4:
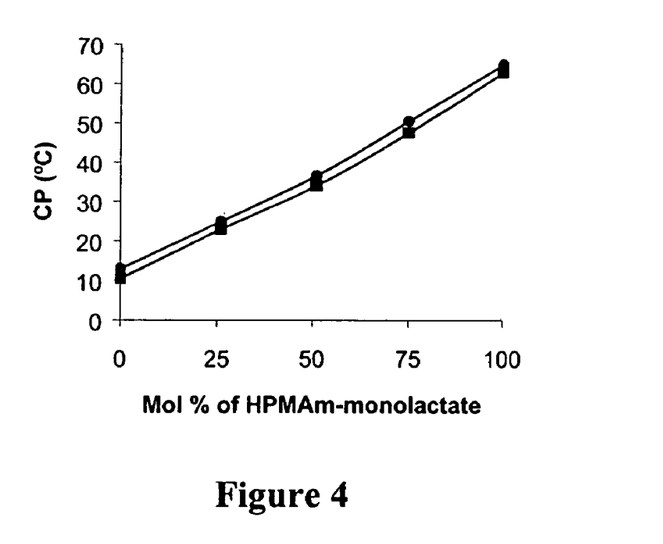
FIG. 4 shows the Cloud Point CP of poly (HPMAm-monolactate-co-HPMAm-dilactate) as a function of the mole-% HPMAm-monolactate in the copolymer is 1 mg/mL solution in water; 1 mg/mL solution in isotonic 120 mM ammonium acetate buffer (pH=5.0).
Figure 5:
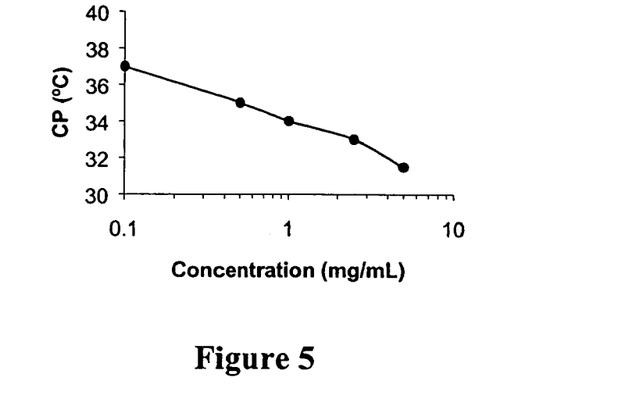
FIG. 5 shows the CP of poly(HPMAm-monolactate-co-HPMAm-dilactate 51/49) in isotonic 120 mM ammonium acetate buffer (pH=5.0) as a function of the polymer concentration.
Figure 6:
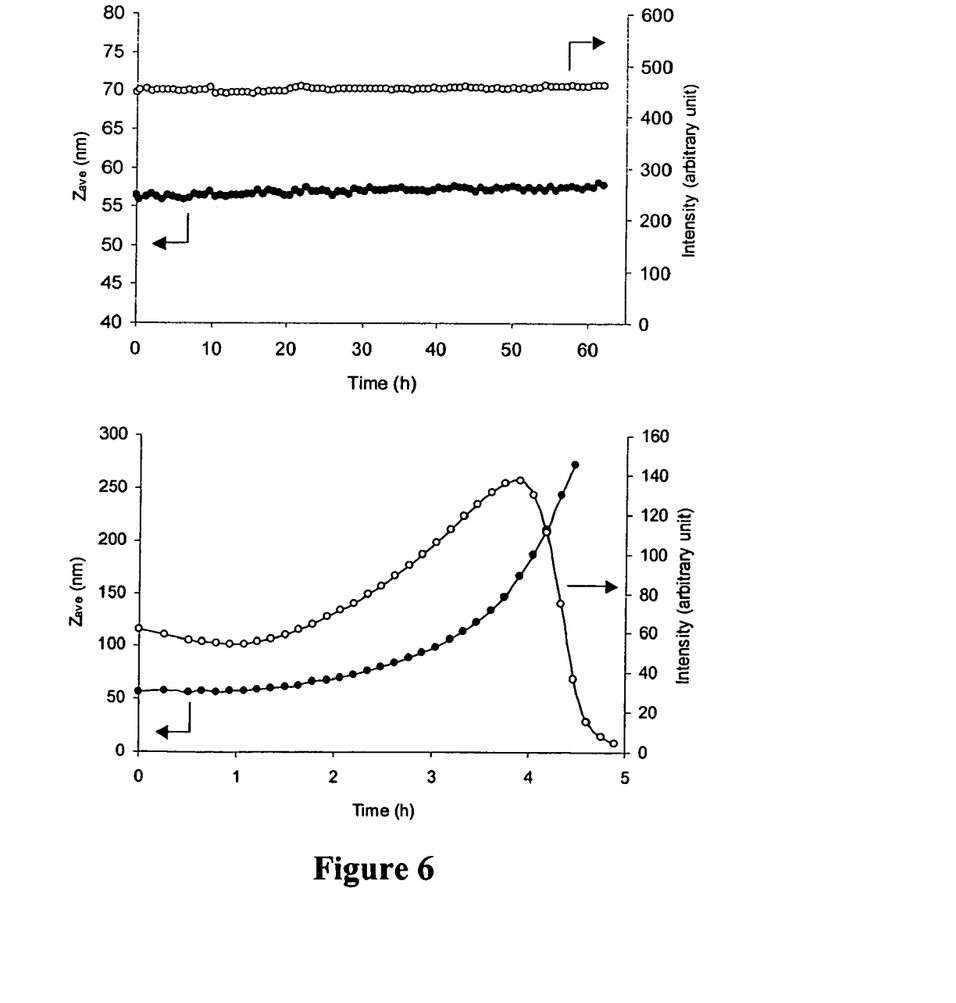
FIG. 6 shows stability data on pHPMAm DL (13600)-6-PEG micelles at 37° C. and at pH=5.0 (top) and pH=9.0 (bottom).

For the copolymers, the composition was close to the feed ratio of the monomers. Static light scattering measurements of these polymers in water and in isotonic 120 mM ammonium acetate buffer (pH=5.0, to minimize hydrolysis of lactate ester side group) were performed. Interestingly, all polymers of Table 1 showed LCST behavior. FIG. 3 shows a typical light scattering intensity-temperature curve for poly(HPMAm-monolactate-co-HPMAm-dilactate) in isotonic 120 mM ammonium acetate buffer (pH=5.0). Poly(HPMAm-monolactate) has a rather high CP (65° C. in water, Table 1) whereas poly(HPMAm-dilactate) has a relatively low CP (13° C. in water, Table 1). This can be explained by the greater hydrophobicity of the dilactate side group over the monolactate side group. Importantly, the CP of the copolymers linearly increased with mol % of HPMA-monolactate monomer (FIG. 4), meaning that the CP of the copolymers can be tailored by the copolymer composition. Although molecular weight of the polymers decreased as the ratio of HPMAm-dilactate increased (Table 1), the decrease of molecular weight is not the reason for the decrease of the CP. Poly(HPMAm-monolactate) with lower molecular weight was prepared and it was observed that the CP slightly increased with the decrease of molecular weight. The CP's in isotonic 120 mM ammonium acetate buffer (pH=5.0) were approximately 2.5° C. lower than those in water (Table 1). This can be attributed to a salting-out effect of ions present in the buffer solution. FIG. 3 shows that thermohysteresis of around 5° C. is observed between the heating and cooling curve. It has been reported that PNIPAAm does not show LCST hysteresis. In contrast, poly(N-isopropylmethacrylamide) shows hysteresis, which is ascribed to the α-methyl group in the polymer backbone resulting in a decreased chain flexibility. Since the polymers of Table 1 also contain α-methyl groups in the polymer backbone, the hysteresis is likely due to the same phenomenon. FIG. 5 shows the effect of the concentration of polymer on the CP. The CP decreased approximately 3° C. as the concentration increased 10-fold. The CP of PNIPAAm is hardly affected by its concentration, while other thermosensitive polymers also show an increase of CP with a decrease in concentration.

The thermosensitive and biodegradable polymers of the invention have attractive features especially as materials for drug delivery and biomedical applications. First, the CP of the polymer can be tailored between 10° C. to 65° C. by the copolymer composition. Second, the lactic acid side groups are removed by hydrolysis in time. This means that the polymer becomes more hydrophilic in time, which is associated with an increase in CP. Therefore, polymers can be designed which are initially in their precipitated form but which become soluble in time. Further, it is expected that the polymers possess a good biocompatibility.

EXAMPLE 2

Paclitaxel (PTX) Loading into pDP2/PG

In this example the loading of PTX into the p(HPMAm-dilactate) 13600/PEG5000 was studied.

First, the polymer was dissolved at a concentration of 10 mg in 1 ml isotonic 120 mM ammonium acetate buffer with a pH of 5.0. The temperature maintained at 0° C. by ice-cooling.

1.8 ml of this polymer solution or of the buffer as a reference was cooled with ice. Next a 0.2 ml PTX solution in ethanol was added meanwhile stirring and ice cooling the solution. To sample A and sample B 10 mg/ml PTX solution was added and to sample C 20 mg/ml. The volume ratio of PTX solution and polymer solution is 1:9. Thus 10% ethanol (V/V) is present in the mixture.

Then the solution was put into a water bath of 50° C. for 1 minute to form micelles. Next the solution was left at room temperature for 1 minute and subsequently filtrated with a 0.45 μm filter to remove precipitated PTX.

The DLS of the filtrate was measured at 25° C. and the amount of PTX by HPLC. The results are in the table below.

Paclitaxel (PTX) Loading into pDP2/PEG

Polymer: p(HPMAm-dilactate)13600/PEG5000

Polymer was dissolved at 10 mg/mL in isotonic 120 mM ammonium acetate buffer (pH 5.0 at 37° C.) with ice-cooling.

Procedures:

Ice-cool 1.8 mL polymer solution or buffer;

Add 0.2 mL PTX solution in ethanol (10 mg/mL for A and B, 20 mg/mL for C) with ice-cooling and stirring (Volume ratio of PTX solution and polymer solution is 1:9, so 10% (v/v) ethanol is in the mixture);

Immediately put this solution to 50° C. to form micelles for 1 min;

Leave the solution to be at room temperature and filtrate with 0.45 µm filter to remove precipitated PTX;

Measure DLS at 25° C. and PTX amount by HPLC tion using HPMAm-dilactate as monomer and PEG$_2$-ABCPA as macroinitiator essentially as described previously for the synthesis of block-copolymers of PEG 5000 and NIPAAm or NIPAAm-HPMAm(-lactate) (Neradovic, D, et al. Thermoresponsive polymeric micelles with controlled instability based on hydrolytically sensitive N-isopropylacrylamide copolymers. *Macromolecules* (2001) 34:7589-7591) and schematically shown in scheme 1.

Scheme 1. Synthesis route and structure of pHPMAmDL-b-PEG block copolymer.

| Sample | A) PTX + buffer | B) PTX 1 mg/mL | C) PTX 2 mg/mL |
|---|---|---|---|
| PTX added (µg/mL) | 1000 | 1000 | 2000 |
| Polymer (mg/mL) | 9 | 9 | 9 |
| % Ethanol in formulation | 10 | 10 | 10 |
| Outlook after forming micelles | lots of precipitates | opalescent | opalescent |
| PTX loaded (µg/mL) | 1.4 | 1003 | 1847 |
| Loading efficiency (%) | | 100.3% | 92.4% |
| Zave (PD) at 25° C. | — | 59 nm (0.059) | 66 nm (0.088) |

From the table it is clear that the amount of loaded PTX increase dramatically and almost linearly with the amount of polymer used. Furthermore, it is indicated that the average particle size Z is well below 100 nm; for sample B 59 nm and for sample C 66 nm, respectively.

EXAMPLE 3

Synthesis of AB Blockcopolymers of p(HPMAm-dilactate) (A-Block) and PEG (B-Block) (p(HPMAm-dilactate)-b-PEG Block Copolymers (pHPMAmDL-b-PEG))

p(HPMAm-dilactate)-b-PEG block copolymers (pHPMAmDL-b-PEG) were synthesized by radical polymerisa- The macroinitiator (PEG 5000)$_2$-ABCPA was synthesized as follows. A 50 mL round bottom flask was loaded with 2 g (0.4 mmol) polyethylene glycol 5000 monomethylether (PEG 5000), 0.056 g (0.2 mmol) 4,4-azobis(4-cyanopentanoic acid) (ABCPA), 0.0189 g (0.06 mmol) 4-(dimethylamino)-pyridinium-4-toluene-sulfonate (DPTS) and 0.125 g (0.6 mmol) N,N'-dicyclohexylcarbodiimide (DCC). The flask was evacuated and filled with nitrogen. Next, 3 mL of 1:1 mixture of dichloromethane (stabilized with amylene) and dry DMF was added using a syringe. The mixture was stirred at room temperature for 24 hours. Next, the reaction mixture was filtered, the solid was washed with dichloromethane and the combined organic solutions were evaporated. Thereafter, the product was dissolved in toluene, remaining insoluble substances were removed by filtration, and the solvent was evaporated. The obtained dry product was extracted with diethyl ether to remove traces of dicyclohexyl urea (DCU). The product obtained was dissolved in water and the solution was filtered to remove remaining solid. The product was collected after freeze-drying (yield 80%). This macroinitiator is used for the synthesis of p(HPMAm-dilactate)-b-PEG block copolymers (pHPMAmDL-b-PEG). In detail: HPMAm-dilactate and PEG$_2$-ABCPA were dissolved at a total concentration of 0.3 g/mL in acetonitrile. To obtain block copolymers with different pHPMAmDL block lengths, the ratio of monomer to macroinitiator was varied between 35/1 to 140/1 (mol/mol). The polymerization was conducted at 70° C. for 24 hours in a nitrogen atmosphere. The polymers were collected by centrifugation after precipitation in diethyl ether. The polymers were further purified by dissolving these in cold water, followed by filtration through a 0.22 µm filter and freeze-drying. The products were characterized by $^1$H NMR (solvent: CDCl$_3$) with a Gemini 300 MHz spectrometer (Varian Associates Inc. NMR Instruments, Palo Alto, Calif.) and gel permeation chromatography (GPC). GPC was carried out using Plgel 3 μm MIXED-D+Plgel 3 μm MIXED-E columns (Polymer Laboratories) and poly(ethylene glycol) standards. The eluent was DMF containing 10 mM LiCl; the elution rate was 0.7 mL/min; and the temperature was 40° C.

$^1$H NMR (solvent: CDCl$_3$) (all protons are from pHP-MAmDL block except for methylene protons from PEG.): δ=6.5 (b, CO—N$\underline{H}$—CH$_2$), 5.0 (b, NH—CH$_2$—C$\underline{H}$(CH$_3$)—O and CO—C$\underline{H}$(CH$_3$)—O), 4.4 (b, CO—C$\underline{H}$(CH$_3$)—OH), 3.6 (b, PEG methylene protons, O—C$\underline{H}_2$—C$\underline{H}_2$), 3.4 (b, NH—C$\underline{H}_2$—CH(CH$_3$)), 2.0-0.6 (the rest of the protons from pHPMAmDL block).

The number average molecular weight ($M_n$) of pHPMAmDL block was determined by $^1$H-NMR as follows: a) the value of the integral of the PEG protons divided by 454 (average number of protons per one PEG 5000 chain) gave the integral value for one PEG proton and b) the number of HPMAmDL units in the polymers was determined from the ratio of the integral of the methine proton (CO—C$\underline{H}$(CH$_3$)—OH) of HPMAmDL to the integral of one PEG proton. The number average molecular weight of the pHPMAmDL block was calculated from the resulting number of units.

Determination of the Critical Micelle Temperature (CMT) of the Different Block Copolymers The CMT of block polymer solution was determined with static light scattering using a Horiba Fluorolog fluorometer (650 nm, at a 90° angle). The polymers were dissolved at a concentration of 10 mg/mL in isotonic 120 mM ammonium acetate buffer (pH=5.0) at 0° C. The scattering intensity was measured every 0.2° C. during heating and cooling (the heating/cooling rate was approximately 1° C./min). Onsets on the X-axis, obtained by extrapolation of the intensity-temperature curves during heating to intensity zero were considered as the CMT. The CMT determinations were done at least two times and the deviations were smaller than 0.5° C.

Formation of Micelles

Micelles of block copolymers were formed by quickly heating an aqueous polymer solution from below to above CMT. The polymers were dissolved at a concentration of between 0.1 to 20 mg/mL in isotonic 120 mM ammonium acetate buffer (pH=5.0) at 0° C. in glass vials. Next, the polymer solution was quickly brought from 0° C. to 50° C. and was left at 50° C. for 1 minute. Before dynamic light scattering measurements, the micelle solution was incubated at 37° C.

Size Measurements of the Micelles

Dynamic light scattering (DLS) measurements were done to determine the size of the micelles, using Malvern 4700 system (United Kingdom) consisting of an Autosizer 4700 Spectrometer, a pump/filter unit, a Model 2013 air-cooler Argon ion laser (75 mW, 488 nm, equipped with a model 2500 remote interface controller, Uniphase) and a computer with DLS software (PCS, version 3.15, Malvern). The measurement temperature was 37° C. and the measurement angle was 90°. The change in solvent viscosity with temperature was corrected by the software.

Determination of the Critical Micelle Concentration (CMC)

The critical micelle concentration (CMC) of the different block copolymers was determined using pyrene as a fluorescence probe. Micelles of block copolymers were formed as described above in isotonic 120 mM ammonium acetate buffer (pH=5.0) at a concentration of 2 mg/mL. The micelle solutions with different polymer concentrations ranging from to 0.00001 mg/mL to 1.0 mg/ml were obtained by diluting the polymer solution with the same buffer at room temperature. Pyrene was dissolved in acetone at $1.8\times10^{-4}$M and 15 μL of this solution was added to 4.5 mL of micelle solution, which gave $6.0\times10^{-7}$ M of pyrene in the mixture. The micelle solutions with pyrene were equilibrated at room temperature in the dark for 20 hours to allow the evaporation of acetone. Fluorescence excitation spectra of pyrene were obtained using a Horiba Fluorolog fluorometer (at a 90° angle). The excitation spectra were recorded at 37° C. from 300 to 600 nm with the emission wavelength at 390 nm. The excitation and emission band slits were 4 nm and 2 nm, respectively. The intensity ratio of 1338/1333 was plotted against polymer concentration to determine the CMC.

Micelle Destabilization

The destabilization of micelles was monitored at two different pHs (5.0 and 9.0). For pH 5.0, micelles of block copolymers were formed as described above in isotonic 120 mM ammonium acetate buffer (pH=5.0) at a concentration of 2 mg/mL. For pH 9.0, samples were prepared as follows. First, the polymers were dissolved in water at 20 mg/mL and then diluted 10-fold with 300 mM NaHCO$_3$ buffer (pH=9.0). Micelles were formed in the same way as described. For both samples, the size change of micelles and the change of scattering intensity in time were measured by dynamic light scattering at 37° C. The results are shown in FIG. 1. This figure shows that under conditions where hydrolysis of the lactic acid side groups is minimized (pH=5) the micelles were stable during the time of the measurements (60 hours). In contrast, at pH 9 a rapid destabilization of the micelles is observed. This destabilization is due to hydrolysis of the lactic acid side groups. This hydrolysis is associated with an increase in hydrophilicity of the thermosensitive block. Once the hydrolysis has proceeded to such an extent that the LCST of this block passes 37° C., the micelles start to dissolve. This happens round 3-4 hours of incubation at 37° C. and pH 9.0. Since the hydrolysis of the lactic acid side groups is first order in hydroxyl ion concentration, a destabilization time of 120-160 hours at pH 7.4 can be expected.

The following table summarizes the characteristics of the different synthesized blockcopolymers.

Characteristics of pHPMAmDL-b-PEG block copolymers

| Polymers | $M_n$[a] | $M_w$[a] | $M_w/M_n$ | CMT (° C.)[b] | CMC (mg/mL)[c] | $Z_{ave}$ (nm)[d] |
|---|---|---|---|---|---|---|
| pHPMAmDL(3000)-b-PEG[e] | 7400 | 10400 | 1.41 | 12.5 | 0.15 | 60 ± 1 |
| pHPMAmDL(6900)-b-PEG[e] | 11900 | 23300 | 1.95 | 7.5 | 0.03 | 51 ± 1 |
| pHPMAmDL(13600)-b-PEG[e] | 15000 | 32800 | 2.18 | 6.0 | 0.015 | 53 ± 1 |

[a] $M_n$ = number average molar weight; $M_w$ = weight average molar weight determined by GPC
[b] Determined by SLS for 10 mg/mL solution in pH 5.0 buffer.
[c] Determined from pyrene excitation spectra at 37° C. in pH 5.0 buffer.
[d] Determined by DLS for 1 mg/mL solution in pH 5.0 buffer.
[e] Number in brackets is $M_n$ of HPMAmDL block determined by $^1$H NMR. $M_n$ of PEG is 5000.

EXAMPLE 4

Hydrogels Based on ABA Blockcopolymers of p(HPMAm-dilactate) (A-Block) and PEG (b-Block)

Hydrogel forming ABA block copolymers of p(HPMAm-dilactate) (A-block) and PEG (b-block) were obtained using the same synthetic strategy as described for the synthesis of AB blockcopolymer (scheme 1). However, instead of the (PEG 5000)$_2$-ABCPA macroinitiator another type of macroinitiator was used. This initiator was synthesized by reaction of normal PEG (instead of monomethoxy PEG) with ABCAPA. In detail: 1 mmol of 4,4-azobis-(4-cyanopentanoic acid) (ABCPA), 3 mmol of N,N'-dicyclohexylcarbodiimide (DCC) and 0.3 mmol 4-(dimethyl-amino)pyridinium-4-toluenesulfonate (DPTS) were dissolved in mixture 1:1 of dry tetrahydrofuran (THF) and dichloromethane. The mixture was stirred at room temperature for 10 to 20 minutes. Next, 1 mmol poly(ethylene glycol) (PEG, number average molar mass 2000 Or 4000) was added. This total mixture was stirred at room temperature for 20 h. Subsequently, the mixture was filtered and the solvent was evaporated. After evaporation, the product was dissolved in water en stirred for couple of hours and filtered to remove DCU. The filtrate was lyophilized to yield the PEG-ABCPA. ABA triblockcopolymers of p(HPMAm-dilactate) (A-block) and PEG (B-block) were obtained as described for the micelle forming AB block copolymers (p(HPMAm-dilactate)-b-PEG block copolymers).

The hydrogel forming properties of the different ABA blockcopolymers were studied using rheological analysis. In detail: 300 mg of polymer was dissolved in 700 µl of 100 mM ammonium acetate buffer pH 5 at 0° C. during 24 h. Next, 60 µl of this polymer solution applied to the rheometer (AR1000N, Ta instruments) equipped with a Cone/plate geometry with a radius of 1 cm and an angle of 1°. The temperature was gradually increased 0° C. to 50° C. at a ramp of 2° C./min. The rheological characteristics of the ample was monitored using a frequency of 1 Hz and a strain of 1%. For further experimental details: see De Jong, S. J. et al. Novel self-assembled hydrogels by stereocomplex formation in aqueous solution of enantiomeric lactic acid oligomers grafted to dextran. *Macromolecules* (2000) 33:3680-3686.

The following table summarizes the results.

| Rheological properties of ABA blockcopolymers (A = pHPMAmdilactate; B = PEG) | | | | | |
|---|---|---|---|---|---|
| Molecular weights (kDa) | | | | | |
| B block | A block | G' at 2° C. | G" at 2° C. | G' at 37° C. | G" at 37° C. |
| 4 | 11 | 6 | 40 | 830 | 1100 |
| 2 | 10 | 2 | 20 | 1600 | 2250 |

G' and G" in Pa · s

The invention claimed is:

1. A controlled release system comprising a temperature sensitive polymer having a lower critical solution temperature (LCST) that changes during incubation in an aqueous medium wherein said temperature sensitive polymer consists of
    (a) a homopolymer formed from monomers consisting of N-(2-hydroxypropyl) methyl acrylamide (lactate)$_n$ where n is 1-10 and n is the same in the monomers that constitute said homopolymer, said homopolymer coupled to a hydrophilic block; or
    (b) an interpolymer formed from monomers consisting of N-(2-hydroxypropyl) methyl acrylamide (lactate)$_n$ where n is 1-10 and n varies in the monomers that constitute the interpolymer, said interpolymer optionally coupled to a hydrophilic block; and
    an active ingredient.

2. The controlled release system of claim 1, wherein the hydrophilic block comprises poly(ethyleneglycol).

3. The controlled release system of claim 2, wherein the system is in the form of a hydrogel or a micelle.

4. The controlled release system of claim 1 which is in the form of a hydrogel or micelle and wherein said temperature sensitive polymer contains said interpolymer wherein the value of n is varied.

5. The controlled release system of claim 4, wherein the interpolymer is coupled to a hydrophilic block.

6. The controlled release system of claim 5, wherein the hydrophilic block comprises poly(ethyleneglycol).

7. The controlled release system of claim 1 further comprising a homing device.

8. The controlled release system of claim 4 further comprising a homing device.

* * * * *